United States Patent [19]

Greene et al.

[11] Patent Number: 5,770,711
[45] Date of Patent: Jun. 23, 1998

[54] POLYSACCHARIDES SUBSTITUTED WITH POLYCARBOXYLATED MOIETIES

[75] Inventors: Sharon Linda Greene, Canton; Rosann Marie Kaylor, Cumming; Kenneth Raymond Smith, Norcross, all of Ga.

[73] Assignee: Kimberly-Clark Worldwide, Inc., Neenah, Wis.

[21] Appl. No.: 723,799

[22] Filed: Sep. 30, 1996

[51] Int. Cl.$^6$ .......................... C08B 11/12; C08B 15/10; C08B 37/00; D21H 13/04

[52] U.S. Cl. ..................... 536/18.6; 162/157.6; 162/177; 536/56; 536/84; 536/88; 536/123.1

[58] Field of Search ............................ 162/177, 70, 146, 162/157.6; 536/18.6, 56, 58, 84, 63, 123, 123.1, 124

[56] References Cited

U.S. PATENT DOCUMENTS

| | | | |
|---|---|---|---|
| 2,852,507 | 9/1958 | Crane et al. | 260/225 |
| 2,852,508 | 9/1958 | Crane et al. | 260/225 |
| 2,856,400 | 10/1958 | Malm et al. | 260/225 |
| 3,008,953 | 11/1961 | Crane et al. | 260/226 |
| 3,816,402 | 6/1974 | Wilkinson | 260/225 |
| 3,956,261 | 5/1976 | Lin | 260/124 |
| 4,260,740 | 4/1981 | Carrington et al. | 536/63 |
| 4,303,676 | 12/1981 | Balazs | 424/359 |
| 4,548,847 | 10/1985 | Aberson et al. | 428/74 |
| 4,555,468 | 11/1985 | Yano et al. | 430/160 |
| 4,605,721 | 8/1986 | Jenkins et al. | 527/312 |
| 4,654,159 | 3/1987 | Bush et al. | 252/95 |
| 4,764,281 | 8/1988 | Elfline | 210/668 |
| 4,800,024 | 1/1989 | Elfline | 210/665 |
| 4,859,758 | 8/1989 | Shalati et al. | 527/313 |
| 5,086,144 | 2/1992 | Shalati et al. | 527/313 |
| 5,147,343 | 9/1992 | Kellenberger | 604/368 |
| 5,183,707 | 2/1993 | Herron et al. | 428/364 |
| 5,225,047 | 7/1993 | Graef et al. | 162/9 |
| 5,292,877 | 3/1994 | Edgar et al. | 536/63 |
| 5,316,623 | 5/1994 | Espy | 162/164.3 |
| 5,466,461 | 11/1995 | della Valle et al. | 424/423 |
| 5,470,964 | 11/1995 | Qin | 536/20 |
| 5,498,705 | 3/1996 | Qin | 536/20 |
| 5,616,568 | 4/1997 | Pouyani et al. | 514/54 |

OTHER PUBLICATIONS

McGraw Hill Dictionary of Chemical Terms, Third Edition. McGraw–Hill, Inc., pp. 282 & 449, (1984).

*Primary Examiner*—John Kight
*Assistant Examiner*—Howard C. Lee
*Attorney, Agent, or Firm*—William E. Maycock

[57] ABSTRACT

A derivatized polysaccharide in which at least a portion of the active hydrogens originally present in the polysaccharide are substituted by monovalent aliphatic groups containing at least two carboxylic acid groups to an extent sufficient to provide a degree of substitution of at least about 0.1. The monovalent aliphatic groups contain from 4 to about 10 carbon atoms. The polysaccharide may be cellulose. At least a portion of the carboxylic acid groups present in the derivatized polysaccharide may be crosslinked permanently or reversibly. The monovalent aliphatic groups containing at least two carboxylic acid groups may be derived from 2,3-epoxysuccinic acid; 1,2-epoxypropane-1,2,3-tricarboxylic acid; 2-(epoxyethyl)-succinic acid; or mixtures thereof. Also provided is a method of preparing a derivatized polysaccharide. The method involves providing a polysaccharide; dispersing the polysaccharide in a strongly alkaline aqueous alcohol solution; adding to the dispersion an excess of an aliphatic polycarboxylic acid having an epoxy group, wherein the aliphatic polycarboxylic acid contains from 4 to about 10 carbon atoms; and heating the dispersion at a temperature and for a time sufficient to permit the reaction of epoxy groups of the aliphatic polycarboxylic acid with active hydrogens present in the polysaccharide to an extent sufficient to result in a degree of substitution of at least about 0.1. The present invention further provides a paper containing an amount of the derivatized cellulose described above sufficient to provide improved strength characteristics to the paper, compared with an otherwise identical paper which lacks the derivatized cellulose.

21 Claims, No Drawings

POLYSACCHARIDES SUBSTITUTED WITH POLYCARBOXYLATED MOIETIES

BACKGROUND OF THE INVENTION

The present invention relates to polysaccharide derivatives. More particularly, the present invention relates to cellulose derivatives.

Superabsorbents are water-swellable, water-soluble organic or inorganic materials capable, under the most favorable conditions, of absorbing at least about 20 times their weight and, more desirably, at least about 30 times their weight in an aqueous solution containing 0.9 weight percent sodium chloride. Absorbents are similar materials, but typically absorb less than about 20 times their weight of the aqueous sodium chloride solution. Superabsorbents and absorbents in general can be natural or synthetic materials. Examples of absorbents include gelatin; alginates; cellulose-based polymers, such as methyl cellulose, hydroxymethyl cellulose, carboxymethyl cellulose, and cellulose acetate phthalate; starch-based polymers, such as carboxymethyl starch; natural gums, such as gum arabic, locust bean gum, carrageenan gum, and xanthan gum; and pectins. Examples of superabsorbents include polymers formed from acid group-containing monomers, such as poly(acrylates), including poly(acrylic acid), poly(methacrylic acid), and the like; poly(ethers); polyacrylamides; poly(vinyl alcohol); maleic anhydride copolymers; poly(vinyl sulfonates); hydrolyzed acrylonitrile-grafted starch; acrylic acid-grafted starch; poly(N-vinylpyrrolidone); poly(2-hydroxyethylacrylate); poly(2-hydroxyethylmethacrylate); copolymers of sodium acrylate and acrylic acid; poly(vinylsulfonic acid); poly(ethylene oxide); block copolymers of ethylene oxide with polyamides, polyesters, and polyurethanes; and salt forms (where appropriate), mixtures, and copolymers of the above. Some of the more common superabsorbents currently in use, particularly in disposable absorbent products, are alkali metal salts of polyacrylic acids.

Superabsorbents are employed in a variety of such disposable absorbent products as diapers; feminine care products, such as sanitary napkins and tampons; adult incontinence products; and the like. While the superabsorbents currently in use are effective, most of them are prepared from synthetic, petrochemical-based materials. Such synthetic materials often are not biodegradable or biodegrade only after relatively long periods of time. Consequently, absorbent materials based on naturally occurring materials are desired, as such materials would be biodegradable, abundant, and renewable, and also may have a lower cost than the synthetic superabsorbents. This is true even if the absorbent materials based on naturally occurring materials were not as absorbent as currently used superabsorbents. The foregoing characteristics of such absorbent materials, i.e., biodegradability, low cost, abundance, and renewability, would permit the use of greater amounts in disposable absorbent products, thereby compensating for lower absorbencies compared to the currently used superabsorbents.

SUMMARY OF THE INVENTION

The present invention addresses some of the difficulties and problems discussed above by providing absorbent materials based on naturally occurring materials. Accordingly, the present invention provides a derivatized polysaccharide in which at least a portion of the active hydrogens originally present in the polysaccharide are substituted by monovalent aliphatic groups containing at least two carboxylic acid groups to an extent sufficient to provide a degree of substitution of at least about 0.1, wherein the monovalent aliphatic groups contain from 4 to about 10 carbon atoms. By way of example only, the polysaccharide may be cellulose. As another example, at least a portion of the carboxylic acid groups present in the derivatized polysaccharide may be crosslinked. As a further example, at least a portion of the carboxylic acid groups present in the derivatized polysaccharide may be reversibly crosslinked. As yet another example, by way of illustration only, the monovalent aliphatic groups containing at least two carboxylic acid groups may be derived from 2,3-epoxysuccinic acid; 1,2-epoxypropane-1,2,3-tricarboxylic acid; 2-(epoxyethyl)succinic acid; or mixture thereof.

The present invention also provides a method of preparing a derivatized polysaccharide. The method involves providing a polysaccharide; dispersing the polysaccharide in a strongly alkaline aqueous alcohol solution; adding to the dispersion an excess of an aliphatic polycarboxylic acid having an epoxy group, wherein the aliphatic polycarboxylic acid contains from 4 to about 10 carbon atoms; and heating the dispersion at a temperature and for a time sufficient to permit the reaction of epoxy groups of the aliphatic polycarboxylic acid with active hydrogens present in the polysaccharide to an extent sufficient to result in a degree of substitution of at least about 0.1. As noted above, the polysaccharide may be, for example, cellulose, and the aliphatic polycarboxylic acid containing an epoxy group may be 2,3-epoxysuccinic acid, 1,2-epoxypropane-1,2,3-tricarboxylic acid, 2-(epoxyethyl)succinic acid, or a mixture thereof. If desired, the resulting derivatized polysaccharide may be washed, typically with an aqueous alcohol solution, to remove excess base and unreacted epoxy-containing aliphatic polycarboxylic acid.

When it is desired to crosslink at least some of the polycarboxylic acid groups present in the derivatized polysaccharide, it may be desirable or necessary to at least partially neutralize the strongly alkaline aqueous alcohol solution after the heating step. It also may be desirable to wash the derivatized polysaccharide with an aqueous alcohol solution to aid in the removal of excess base, salts resulting from the foregoing neutralization, and unreacted epoxy-containing aliphatic polycarboxylic acid.

Crosslinking typically is carried out by dispersing the derivatized polysaccharide in aqueous alcohol and adjusting the pH of the dispersion to a value of from about 4 to about 9, although in some instances lower or higher pH values may be appropriate. By way of example, the pH of the dispersion may be adjusted to a value of from about 7 to about 9. Crosslinking generally is carried out by methods which are well known to those having ordinary skill in the art. Such methods include, by way of illustration, treatment with heat; glyoxal; glutaric dialdehyde; polyethylene glycol digycidyl ethers; and trivalent metal salts, such as monobasic aluminum acetate. If it is desired to have a reversibly crosslinked derivatized polysaccharide, crosslinking may be carried out by heating the dispersion of the derivatized polysaccharide at a temperature and for a time to effect crosslinking. The crosslinks resulting from a heat treatment may be reversed readily by, for example, treatment with a base, such as sodium hydroxide solution. Alternatively, reversible crosslinking may be achieved by treating the derivatized polysaccharide with a trivalent metal compound for a time and under conditions sufficient to accomplish crosslinking. For example, the trivalent metal compound may be monobasic aluminum acetate. The resulting crosslinks may be reversed by, for example, treatment with a complexing agent, such as ethylenediamine tetraacetic acid, disodium salt.

The present invention further provides a paper containing an amount of a derivatized cellulose prepared in accordance with the present invention sufficient to provide improved strength characteristics to the paper, compared with an otherwise identical paper which lacks the derivatized cellulose. Thus, the derivatized cellulose is a cellulose in which at least a portion of the active hydrogens originally present in the cellulose are substituted by monovalent aliphatic groups containing at least two carboxylic acid groups to an extent sufficient to provide a degree of substitution at least about 0.1, wherein the monovalent aliphatic groups contain from 4 to about 10 carbon atoms. For example, the amount of derivatized cellulose present in the paper may be in a range of from about 2 to about 35 percent by weight, based on the total weight of the paper. As another example, at least a portion of the carboxylic acid groups present in the derivatized cellulose may be crosslinked. As a further example, at least a portion of the carboxylic acid groups present in the derivatized cellulose may be reversibly crosslinked.

DETAILED DESCRIPTION OF THE INVENTION

The terms "polysaccharide" and "original polysaccharide" are used interchangeably herein to mean a polymer composed of a plurality of monosaccharides or other repeating units, such as disaccharides, which may be the same or different. The polysaccharide (or original polysaccharide) is the material from which the derivatized polysaccharide of the present invention is obtained. The polysaccharide may be a naturally occurring material or a modified naturally occurring material. The polysaccharide also may be a synthetic material, although a synthetic material is not desired because of the abundance of suitable naturally occurring polysaccharidens.

By definition, each monosaccharide (or disaccharide or other repeating unit) contains at least one functional group having an "active hydrogen," i.e., a hydrogen atom which is capable of being replaced by another atom or by a group of atoms. The functional group typically found in a monosaccharide or disaccharide is the hydroxy group. However, other groups having an active hydrogen may be present in addition to, or in place of, a hydroxy group. Thus, a polysaccharide by definition contains a plurality of groups having active hydrogens. For convenience, the term "group" is used herein to mean a group of atoms which is present in a polysaccharide, such as a hydroxy group or a hydroxymethyl group. The group of atoms replacing an active hydrogen to form a derivatized polysaccharide is referred to herein as a "moiety."

Examples of polysaccharides include, by way of illustration only and without limitation, cellulose, starch, chitosan, carageenan, natural gums, hydroxymethyl cellulose, and hydroxyethyl cellulose.

As used herein, the term "degree of substitution" is an indication of how many of the active hydrogens present in each repeating unit of the polysaccharide have been replaced or substituted. Thus, the maximum degree of substitution for a given polysaccharide is the number of active hydrogens present in the repeating unit.

As already stated, the present invention provides a derivatized polysaccharide in which at least a portion of the active hydrogens originally present in the polysaccharide are substituted by monovalent aliphatic groups containing at least two carboxylic acid groups to an extent sufficient to provide a degree of substitution of at least about 0.1, wherein the monovalent aliphatic groups contain from 4 to about 10 carbon atoms. By way of example only, the polysaccharide may be cellulose. As another example, at least a portion of the carboxylic acid groups present in the derivatized polysaccharide may be crosslinked. As a further example, at least a portion of the carboxylic acid groups present in the derivatized polysaccharide may be reversibly crosslinked. As yet another example, by way of illustration only, the monovalent aliphatic groups containing at least two carboxylic acid groups may be derived from 2,3-epoxysuccinic acid; aconitic epoxide or 1,2-epoxypropane-1,2,3-tricarboxylic acid; 2-(epoxyethyl)succinic acid; or mixtures thereof.

The present invention also provides a method of preparing a derivatized polysaccharide. The method involves providing a polysaccharide; dispersing the polysaccharide in a strongly alkaline aqueous alcohol solution; adding to the dispersion an excess of an aliphatic polycarboxylic acid (or salt thereof) having an epoxy group, wherein the aliphatic polycarboxylic acid contains from 4 to about 10 carbon atoms; and heating the dispersion at a temperature and for a time sufficient to permit the reaction of epoxy groups of the aliphatic polycarboxylic acid with active hydrogens present in the polysaccharide to an extent sufficient to result in a degree of substitution of at least about 0.1. As noted above, the polysaccharide may be, for example, cellulose, and the aliphatic polycarboxylic acid containing an epoxy group may be 2,3-epoxysuccinic acid, 1,2-epoxypropane-1,2,3-tricarboxylic acid, 2-(epoxyethyl)succinic acid, or a mixture thereof. If desired, the resulting derivatized polysaccharide may be washed, typically with an aqueous alcohol solution, to remove excess base and unreacted epoxy-containing aliphatic polycarboxylic acid.

When it is desired to crosslink at least some of the polycarboxylic acid groups present in the derivatized polysaccharide, it may be desirable or necessary to at least partially neutralize the strongly alkaline aqueous alcohol solution after the heating step. It also may be desirable to wash the derivatized polysaccharide with an aqueous alcohol solution to aid in the removal of excess base, salts resulting from the foregoing neutralization, and unreacted epoxy-containing aliphatic polycarboxylic acid.

Crosslinking typically is carried out by dispersing the derivatized polysaccharide in aqueous alcohol and adjusting the pH of the dispersion to a value of from about 4 to about 9, although in some instances lower or higher pH values may be appropriate. By way of example, the pH of the dispersion may be adjusted to a value of from about 7 to about 9. Crosslinking generally is carried out by methods which are well known to those having ordinary skill in the art. Such methods include, by way of illustration, treatment with heat; glyoxal; glutaric dialdehyde; polyethylene glycol digycidyl ethers; and trivalent metal salts, such as monobasic aluminum acetate. If it is desired to have a reversibly crosslinked derivatized polysaccharide, crosslinking may be carried out by heating the dispersion of the derivatized polysaccharide at a temperature and for a time to effect crosslinking. The crosslinks resulting from a heat treatment may be reversed readily by, for example, treatment with a base, such as sodium hydroxide solution. Alternatively, reversible crosslinking may be achieved by treating the derivatized polysaccharide with a trivalent metal compound for a time and under conditions sufficient to accomplish crosslinking. For example, the trivalent metal compound may be monobasic aluminum acetate. The resulting crosslinks may be reversed by, for example, treatment with a complexing agent, such as ethylenediamine tetraacetic acid, disodium salt.

The present invention further provides a paper containing an amount of a derivatized cellulose prepared in accordance with the present invention sufficient to provide improved strength characteristics to the paper, compared with an otherwise identical paper which lacks the derivatized cellulose. Thus, the derivatized cellulose is a cellulose in which at least a portion of the active hydrogens originally present in the cellulose are substituted by monovalent aliphatic groups containing at least two carboxylic acid groups to an extent sufficient to provide a degree of substitution at least about 0.1, wherein the monovalent aliphatic groups contain from 4 to about 10 carbon atoms. For example, the amount of derivatized cellulose present in the paper may be in a range of from about 2 to about 35 percent by weight, based on the total weight of the paper. As another example, at least a portion of the carboxylic acid groups present in the derivatized cellulose may be crosslinked. As a further example, at least a portion of the carboxylic acid groups present in the derivatized cellulose may be reversibly crosslinked.

The present invention is further described by the examples which follow. Such examples, however, are not to be construed as limiting in any way either the spirit or the scope of the present invention.

EXAMPLES

Procedures

Determination of Decree of Substitution (D.S.)

The procedure is a modification of ASTM Method No. D1439-83a. A 1–3 gram sample of the derivatized polysaccharide was converted into the acid form by adjusting the pH to approximately 2, and allowing the polymer to soak for at least 2 hours. The polymer then was filtered using a 74-micrometer opening nylon mesh screen and washed with about two 100-ml volumes of a 50/50 by volume 2-propanol/water mixture and once with about two 100-ml volumes of 2-propanol. The pulp was air-dried, then oven-dried at 105°–110° C. for about 4 hours. A 0.2–0.6 gram portion of the pulp was accurately weighed into a 25-ml Erlenmeyer flask. A 25-ml aliquot of distilled water was added with 25.0 ml of 0.1N sodium hydroxide solution and the pulp shaken to mix thoroughly. The pulp slurry was heated to boiling with stirring, and allowed to boil for 20 minutes. After 20 minutes, 5 drops of 1% phenolphthalein solution were added to the flask. While still hot, the slurry was titrated with 0.1N hydrochloric acid until the pink solution became clear. Blanks were done at the same time using 25 ml of distilled water and 25.0 ml of 0.1N sodium hydroxide solution.

By way of example, the degree of substitution for pulp derivatized with 2,3-epoxysuccinic acid was calculated as follows:

$$D.S.=0.162A/(2-0.13A)$$

where

A=milliequivalents acid/g pulp or [(ml NaOH)(N NaOH) −(ml HCl)(N HCl)]/weight of sample;

0.162=g/mmole of unmodified or original cellulose;

2=number —COOH groups/moiety; and 0.130=g/mmole of group added to cellulose.

Absorbency Measurements
Saline Retention Value (SRV) Test

The SRV was determined as described in U.S. Pat. No. 4,5448,847 to Aberson and Ring (which is incorporated herein by reference), except that sample size varied from about 0.1 to about 0.3 g, the volume of saline in which the sample was soaked was 100 ml, soak time was 30 minutes, and centrifugation was carried out for 30 minutes. The SRV was calculated as follows:

$$SRV=(wet\ weight-dry\ weight)/dry\ weight$$

Absorbency Under Load (AUL)

A simplified version of the AUL test described in U.S. Pat. No. 5,147,343 to Kellenberger was employed, which patent is incorporated herein by reference. The test was conducted under an approximately zero load or a load of about 0.3 psi (21,000 dynes per cm$^2$). The apparatus for holding the derivatized cellulose was made from one-inch (2.54-cm) inside diameter thermoplastic tubing (referred to hereinafter as the "cylinder") which had been machined out slightly to be sure of concentricity. A 100 mesh stainless steel wire cloth then was fused onto the bottom of the cylinder by heating the wire cloth in a flame until red hot and holding it against the bottom of the cylinder until cool. A soldering iron may be utilized to finish the seal if complete sealing was not achieved or if the seal breaks during testing. Care must be taken to maintain a flat, smooth bottom and not distort the inside of the cylinder. A 4.4-g piston was made of Plexiglass and machined to fit closely in the cylinder without binding in the cylinder. For the 0.3 psi test, a standard 100-g weight was placed on top of the piston to provide a restraining load approximating that experienced in infant diapers. Unless specified otherwise, a sample of derivatized cellulose (about 0.16.g) was utilized which corresponded to a layer of at least about 300 grams per square meter (gsm). The sample to be tested was taken from derivatized cellulose particles which were pre-screened through a U.S. Standard No. 30 mesh and retained on a Standard No. 50 mesh. The particles were pre-screened by hand or automatically with, for example, a Ro-Tap Mechanical Sieve Shaker, Model B, available from W. S. Tyler, Inc., Mentor, Ohio. The desired amount of particles were weighed out on a weighing paper to determine the dry weight and placed on the wire cloth at the bottom of the cylinder. The cylinder was shaken to level the particles on the wire cloth. Care was taken to be sure no particles were clinging to the inside wall of the cylinder. The piston was carefully placed in the cylinder on the particles. If appropriate, the weight was placed on top of the piston. The cylinder was placed in a petri dish which then was filled to a height of 2 mm with saline. The cylinder was allowed to stand in the dish for one hour. The cylinder was removed and the particles were carefully removed and weighed to determine the wet weight. The AUL value was calculated as follows:

$$AUL=(wet\ weight-dry\ weight)/dry\ weight$$

Viscosity Measurements

About 1 g of derivatized pulp, based on the oven-dry weight, was mixed in a Waring® blender with distilled water, unless the pulp was water soluble, in which case methanol/water was used. The resulting slurry was filtered in a Buchner funnel with filter paper to form a thin pulp pad. The pulp pad was rinsed twice with 12.5-ml portions of methanol, after which the pulp was dried at 105° C. for about three hours. Into an aluminum pan was weighed a 0.2500-g sample of the dried pulp; drying was continued until a constant weight of the sample was achieved. The weighed sample of pulp was placed in a Nalgene® bottle containing 10 g of glass beads. Distilled water, 25.0 ml, was pipetted into the bottle which then was flushed with nitrogen; the bottle was shaken vigorously for one minute. The bottle then was charged by pipette with 25.0 ml of 1M cupriethylene diamine ("cuen") solution, flushed with nitrogen, and shaken vigorously for 15 seconds. The bottle then was shaken at high speed on a wrist shaker for five minutes and allowed to stand for five minutes. The resulting solution was transferred to a clean size 200 Cannon-Fenske type viscometer and the viscometer placed in a constant temperature bath (Model M-1, Cannon Instrument Company, State College and Boalsburg, Pa.) set at 25° C. The viscometer and its contents were allowed to equilibrate for five minutes. Viscosity measurements then were taken with a stopwatch in accordance with the viscometer manufacturer's instructions.

ESA Pulp Preparations 2,3-Epoxysuccinic acid (ESA) pulps were prepared by derivatizing cellulose pulp as described in the following examples. The procedures often used the same pretreatments to make the pulp more reactive or susceptible to modification; these pretreatments are described first.

Pretreatment A

Samples of never-dried Kraft mixed southern softwood (CR-054), obtained from the Coosa Pines, Alabama mill of Kimberly-Clark Corporation, were diluted from approximately 30 percent by weight solids to about 10 percent by weight solids by adding 150 ml of distilled water to 75 g of wet pulp. The mixture was stirred by using a stirring rod for the softwood pulp and gentle hand-mixing for the hardwood pulp to break apart large clumps. Each sample then was placed in the center of a commercial disc refiner which was rotated briefly to distribute the fiber around the sides, then rotated further to more carefully distribute pulp evenly. After turning on the refiner, the teeth were engaged. The revolution counter was set to zero and recorded. A total of 5500 revolutions was used for most derivatized cellulose preparations. This procedure gave an average freeness value in accordance with TAPPI procedure T2.27 OS-58 of 428 ml for CR-054 pulp.

Pretreatment B

In a typical procedure, 54.5 g of CR-054 pulp was added to a solution of 10 percent by weight sodium hydroxide in a 2-liter resin kettle equipped with a stirrer and nitrogen purge. The resin kettle was heated to 40° C. for four hours by means of a water bath. The slurry was filtered, washed, and soaked to separate the hemicellulose and base (in the filtrate) from the cellulose. After multiple washings (6-7 liters, total), the pH of the pulp was neutral. The pulp then was solvent exchanged by soaking and rinsing four times with 300-ml portions methanol. The pulp was air dried at room temperature (about 20°–25° C.), and vacuum dried at room temperature over phosphorus pentoxide ($P_2O_5$) for 5 hours. The percentage weight loss was recorded and was typically 14 percent.

Pretreatment C

The CR-054 pulp was solvent exchanged, first with methanol and then with 2-propanol, by soaking and rinsing four times with 300-ml portions of each solvent. A Kitchenaid® mixer was used to aid with the distribution of solvent each time. After the final filtration, the 2-propanol/cellulose pulp pad was weighed, and 2-propanol was added to bring the percent solids to 12.4 percent.

Pretreatment D

The amount of CR-054 pulp before solvent exchange (Pretreatment C) was 43.4 g of 34.6 percent solids (15.0 g, 0.093 mole, dry weight). The total weight after solvent exchange of cellulose with 2-propanol was 121 g. To this amount of pulp was added 22.7 g of sodium hydroxide dissolved in 29 ml of deionized water. The resulting mixture was allowed to soak for 16 hours, after which time 76 g of 2-propanol was added. The mixture was allowed to stand for two hours under a nitrogen atmosphere. The mixture then was filtered through a 74-micrometer opening mesh screen using a Buchner funnel and a side-arm flask attached to a vacuum, followed by application of a latex rubber dam over the filter cake while continuing suction for approximately one minute.

EXAMPLE 1

This example describes the preparation of an 2,3-epoxysuccinic acid-derivatized pulp having a low degree of substitution.

The 2,3-epoxysuccinic acid monosodium salt was prepared as follows. A 250-ml, round-bottomed, three-necked flask was equipped with a stirrer and fittings for a pH probe and a temperature probe. Temperature and pH were monitored after the addition of each reagent and throughout the reaction. The flask was charged with 75 ml of distilled water and 29 g (0.25 mole) of maleic acid. The mixture was stirred to dissolve the maleic acid, after which 30 g (0.375 mole) of 50 percent aqueous sodium hydroxide solution was added to the flask. The clear reaction solution immediately became cloudy and heat was generated. Three to five minutes later, sodium tungstate (1.65 g, 0.005 mole) was added. Thirty percent hydrogen peroxide then was added as a single aliquot (28.9 g, 0.25 mole). The pH of the reaction mixture was adjusted to 5–6 with additional sodium hydroxide solution (4.5 g, 0.056 mole). The reaction mixture was heated for 20 minutes to 58°–60° C. and the heat source was removed from the flask. The solution started to clear with the formation of bubbles. As soon as the temperature of the reaction solution approached 95° C. (five minutes later), the flask was quickly immersed in an ice bath. When the temperature of the reaction solution reached 50°–60° C., the pH of the solution was adjusted to 4–5 with sodium hydroxide solution. The monitoring of the pH and temperature is shown below in Table A.

TABLE A

| Event | pH | Temp, °C. |
| --- | --- | --- |
| Dissolution of maleic acid | 0.8 | 16.5 |
| Addition of sodium hydroxide | 2.8 | 51.1 |
| Addition of sodium tungstate | 3.4 | 38.2 |
| Addition of hydrogen peroxide | 2.9 | 32.1 |
| Addition of sodium hydroxide | 5.1 | 33.5 |
| Started heating | 5.0 | 34.3 |
| Removed heat | 3.0 | 52.9 |
| Placed flask in ice bath | 3.0 | 90.0 |
| pH adjustment with sodium hydroxide | 5.6 | 28.0 |

The reaction solution was evaporated under reduced pressure to give 34 g of 2,3-epoxysuccinic acid monosodium salt having a purity of 96 percent as determined by $^{13}C$ NMR. No attempt was made to purify the product.

Pretreatments A, B, and C were carried out sequentially. Cellulose CR-054 pulp, 76 g having a consistency of 19.7 percent, equivalent to 15 g on a dry-weight basis, was solvent exchanged (Pretreatment C), filtered, weighed, and placed in a resin kettle containing approximately 8 g (0.33 mole) of sodium hydride in excess 2-propanol. No water was added to the reaction mixture. The reaction mixture was heated to 60° C., during which time the reaction mixture went from an opaque gray color to clear. To the reaction mixture then was added 28.4 g (0.185 mole) of 2,3- epoxysuccinic acid monosodium salt. Heating of the reaction mixture at 60° C. was continued with the occasional addition of 2-propanol to replace evaporated solvent. After six hours, the reaction was halted by the addition to the reaction mixture of 17.8 g (0.33 mole) of ammonium chloride to neutralize the base present. After thorough stirring by means of Kitchenaid® mixer, the reaction mixture was allowed to stand several days. The product was worked up by adding a molar excess (30.4 g, 0.57 mole) of ammonium chloride to neutralize the base. A 300-ml aliquot of 2-propanol was added and the product was filtered through a 74-micrometer mesh nylon screen using a Buchner funnel with side-arm flask attached to a vacuum source. The product was washed five times with water and 2-propanol as follows:
First wash: 200 ml of water and 500 ml of 2-propanol;
Second wash: 100 ml of water and 300 ml of 2-propanol;
Third wash: 100 ml of water and 300 ml of 2-propanol;
Fourth wash: 100 ml of water and 300 ml of 2-propanol; and
Fifth wash: 200 ml of 2-propanol. Each wash was done with stirring and soaking between each followed by vacuum filtration. The resulting product was air dried to give 14 g (87 percent yield) of a derivatized cellulose having a degree of substitution of 0.07. The AUL values at 0.3 psi and 0 psi were 8 and 11 g saline/g, respectively.

EXAMPLE 2

This example describes the preparation of a 2,3-epoxysuccinic acid-derivatized pulp (CR-054) having a moderate degree of substitution.

The procedure of Example 1 was repeated, except that Pretreatment B was employed, followed by Pretreatment D. The pretreated pulp plus an additional 76 g of 2-propanol were charged into a Helicone® mixer (Model 2CV Mixer, Atlantic Research Corporation; the bowl assembly of the mixer has a capacity of 250–300 ml. and is jacketed to permit temperature control by a Brookfield EX-200 Constant Temperature Circulating Water Bath). The contents of the mixer were heated to 60° C. by means of a circulating water bath. Disodium 2,3-epoxysuccinate (70 percent purity, Aldrich Chemical Company, Inc., Milwaukee, Wis.), 32.5 g (0.13 mole) was added over a period of 30 minutes. Heating was continued for six hours with occasional stirring (about 3–5 minutes every hour), and the reaction mixture was allowed to cool overnight.

The reaction mixture was filtered and an aliquot of the filtrate was titrated with acid. From such titration, it was calculated that the pulp still contained 0.93 mole of base. Concentrated hydrochloric acid, 93 g (0.093 mole) diluted with about 200 ml of 2-propanol was slowly added to the pulp product while being mixed in a blender. The pulp dispersion was very acidic after only half of the acid solution had been added. Approximately 200 ml of water was added, after which the mixture was filtered on a 20-micrometer nylon mesh screen. The isolated pulp was placed in a Soxhlet thimble and extracted with a 2-propanol/water mixture (600 ml of an 88/12 w/w mixture) for 12 hours to give 8 g (46 percent yield) of derivatized cellulose pulp having a degree of substitution of 0.28.

EXAMPLE 3

This example describes the preparation of another 2,3-epoxysuccinic acid-derivatized pulp having a moderate degree of substitution.

Pretreatments A, B, C, and D were conducted sequentially on the CR-054 pulp. The pulp then was transferred to the pre-heated Helicone® mixer with 76 g of 2-propanol. 2,3-Epoxysuccinic acid monosodium salt (28.52 g) was added in three approximately equal portions. The reaction was maintained between 56°–65° C. for 7 hours with constant stirring. Twenty percent water/2-propanol (100 ml) was added and the mixture was allowed to soak. The mixture then was worked up as described in Example 1. The air-dried product weighed 23.9 g. AUL values (0.3 psi and 0 psi) were 13 and 19 g saline/g, respectively. The D.S. was 0.31.

EXAMPLE 4 s example describes the preparation of a 2,3-epoxysuccinic acid-derivatized pulp having a low to moderate degree of substitution and the use of such pulp as an additive in the preparation of paper handsheets.

Preparation of Derivatized Pulp

Never-dried CR-054 pulp, 53.8 g (equivalent to 19.9 g on an oven-dried basis), was mixed with 1 liter of 10 percent by weight sodium hydroxide solution and heated for four hours at 60° C. with stirring under a nitrogen atmosphere. The mixture was allowed to cool to room temperature for one hour, filtered, and rinsed with four 300-ml portions of distilled water. The wet pulp was solvent exchanged with methanol (about four 300-ml rinses), air dried, then dried under vacuum over $P_2O_5$.

A 15-g portion of the dried pulp was placed in a 500-ml Erlenmeyer flask containing 106 g of 2-propanol. A sodium hydroxide solution consisting of 22.7 g (0.57 mole) of sodium hydroxide and 29.1 g or water was added to the flask with mixing. The flask was stoppered and the pulp was allowed to swell overnight. To the flask then was added 76 g of 2-propanol and the pulp was allowed to swell for another 1.75 hours. The pulp was isolated by filtration and added to the Helicone® mixer with an additional 76 g of 2-propanol.

The addition of disodium 2,3-epoxysuccinate (Aldrich Chemical Company, Inc.) was started with a 10-g portion, followed by stirring for five minutes. After one hour, heating of the reaction mixture to 60° C. was started and another 1 0-g portion of the 2,3-epoxysuccinate was added, again followed by stirring for five minutes. Twenty minutes later the remaining 12.5 g of the 2,3-epoxysuccinate was added with five minutes stirring. The total amount of disodium 2,3-epoxysuccinate added was 32.5 g or 0.13 mole. The reaction mixture then was heated at 60° C. for a total of 9.5 hours, with a total of about 25 minutes stirring time. The resulting derivatized pulp was converted to the acid form by adding 3N hydrochloric acid until the pH was 1–2 as measured by pH paper. After soaking for two hours, 2-propanol was added to the acidic pulp and the pulp was collected on a 20-micrometer nylon mesh screen. The pulp then was rinsed with four 2-propanol/water rinses (about 80/20 v/v) by first mixing the pulp with water and then adding the 2-propanol to allow the pulp to be more easily filtered between each rinse. One final rinse was done with 2-propanol, and the derivatized pulp was air dried to give 17.1 g in essentially quantitative yield. The derivatized pulp had a D.S. of 0.18.

Handsheet Preparation

TAPPI Procedure No. T205 om-88 was followed with a few modifications. A separate portion of pulp was taken to determine the percent solids of the pulp. Using that value, enough pulp to provide 24 g on an oven-dry basis was placed in the disintegrator bowl with 2,000 ml total water (i.e., 2,000 ml less the amount of water already present in the pulp). The resulting pulp slurry was disintegrated at 3,000 rpm for 50,000 revolutions using a disintegrator manufactured by Century Electric Inc. (Catalog No. C664, St. Louis, Mo.). The disintegrated pulp was poured into a clean plastic bucket and diluted to 13.5 liters with distilled water. The resulting diluted pulp slurry was stirred with a mechanical stirrer (stainless steel paddle) at 800 rpm for 5 minutes. Stirring was continued throughout the papermaking process to ensure that the slurry remained homogeneous. A Teflon° mesh screen with 74-micrometer openings was placed on top of the standard wire mesh of the sheet forming machine (Type 10-1, Lorentzen and Wettre, Stockholm, Sweden). The machine was half-filled with tap water, then two 400-ml aliquots of the diluted pulp slurry were added. Sufficient additional tap water was added to bring the surface of the machine contents to the mark on the sheet machine (349.3 mm above the wire mesh on the bottom surface). The slurry was mixed in the sheet forming machine as described in the TAPPI test procedure using the standard perforated stirrer. After a pause of 4-6 seconds, the drain cock of the machine was fully opened, letting all the water drain under suction to form the handsheet. Each handsheet then was couched (or blotted) and pressed as described in steps 7.3.2–7.5.2 of the TAPPI procedure, using a press manufactured by Testing Machine Inc., Amityville, N.Y. The handsheets were stacked in drying rings to air-dry overnight. Once dry, the handsheets were oven-heated at varying temperatures and times to promote crosslinking and evaluate the effect that this would have on tensile strength.

Tensile Testing

An Instron Model 1122 Universal Testing Instrument (Instron Corporation, Canton, Mass.) with a 50-kg load cell was employed to determine the tensile strengths of the handsheets. Four one-inch (about 2.5-cm) strips were traced with a pencil in the center of each 6-inch (about 15-cm) diameter handsheet. The strips were cut out of the handsheet using a paper cutter.

Both dry and wet tensile testing were carried out. For both tests, the following instrument parameters were employed:
Crosshead speed: 0.5 inch/minute (about 0.2 mm/second) (set with pre-set speed 122 with a 20:1 crosshead speed reducer)
Gauge length: 4 inches (about 10 cm)
Sample width: 1 inch (about 2.5 cm)
Jaw pressure: 60–65 pounds per square inch (about 4.2–4.6 kg per cm$^2$)

The full scale load (i.e., the upper limit of the chart recorder) was 10 kilograms force (kgf) for dry tensile testing and 1 kgf for wet tensile testing. Dry tensile testing utilized a single strip. Wet tensile testing was conducted by stacking three on the strips on top of each other, quickly immersing the stacked strips in water, and immediately blotting the stack between two sheets of the standard blotting paper employed in the preparation of the handsheets.

Handsheets containing only CR-054 pulp and handsheets composed of 95 percent by weight of CR-054 pulp and 5 percent by weight of the derivatized pulp of this example were prepared and tested for both dry and wet tensiles. Various drying or curing temperatures of the handsheets were investigated. The results are summarized in Table 1. In the table, results for handsheets containing only CR-054 pulp are shown in the "Control" column and results for handsheets containing 5 percent by weight of the derivatized pulp of this example are shown in the "5% ESA" column. In addition, the percent differences of the 5% ESA values relative to the control values are shown in the "PD" (percent difference) columns (negative differences are shown in parentheses).

TABLE 1

Summary of Handsheet Tensile Results

| Oven Cure | | Dry Tensile (kgf) | | | Wet Tensile (kgf) | | |
|---|---|---|---|---|---|---|---|
| Hrs. | °C. | Control | 5% ESA | PD | Control | 5% ESA | PD |
| 3 | 105 | 5.7 | 6.3 | 10 | 0.44 | 0.46 | 5 |
| 24 | 105 | 6.1 | 6.2 | 2 | 0.52 | 0.58 | 12 |
| 3 | 115 | 6.6 | 6.8 | 3 | 0.52 | 0.53 | 2 |
| 24 | 115 | 6.4 | 6.9 | 8 | 0.60 | 0.75 | 25[b] |
| 24 | 115 | 6.3 | 7.0 | 11[a] | 0.66 | 0.92 | 39[b] |
| 1 | 150 | 6.4 | 6.4 | 0 | 0.65 | 0.84 | 29[b] |
| 1 | 150 | 6.3 | 6.2 | (2) | 0.66 | 0.87 | 32[b] |

[a]In accordance with a student t-test, a statistically significant difference was found at the 95% confidence level.
[B]In accordance with a student t-test, a statistically significant difference was found at the 99% confidence level.

The data in Table 1 suggest that the inclusion in paper handsheets of 5 percent by weight of a derivatized cellulose having a D.S. of 0.18 has little or no effect on dry tensile values. However, such inclusion clearly results in a statistically significant increase in wet tensile values, with the increases typically being in a range of from about 25 to about 40 percent.

EXAMPLE 5

This example describes the preparation of a derivatized pulp as an in situ reaction by reparing the derivatizing agent (2,3-epoxysuccinic acid) in the presence of the cellulose. Two different reaction conditions were explored, namely, acidic (pH 4) and (pH 12.4).

Ultranier J cellulose, 75.1 g (20.8 g dry weight, 0.13 mole) was soaked overnight in 20 percent by weight aqueous sodium hydroxide, filtered, washed with approximately 1 liter of distilled water, and filtered again. The swollen, filtered cellulose was placed in a 250-ml resin kettle equipped with a heating mantle. The kettle then was charged with 42.2 g (0.36 mole) of maleic acid dissolved in 100 ml of water. The pH of the resulting mixture was about 1.4. The resin kettle then was charged with 42.8 g (0.54 mole) of a 50 percent by weight sodium hydroxide solution which caused the temperature of the reaction mixture to rise to about 62° C. Disodium tungstate, 2.4 g, then was added, followed almost an hour later by the addition of 41.09 g (1.21 moles) of 30 percent hydrogen peroxide solution. The reaction mixture then was heated to about 60° C. over a period of about an hour, after which the mixture was cooled by placing the resin kettle in an ice bath. After cooling, the reaction mixture was allowed to stand overnight and a small sample of the mixture removed.

The reaction mixture was divided into two approximately equal portions. The first portion had a pH of 3.97 and was heated at 70° C. for six hours. The end pH was 4.07. To the second portion was added 10.9 g of 50 percent aqueous sodium hydroxide solution to give a reaction mixture pH of 12.4. The reaction mixture was heated at about 75° C. for six hours. Each reaction mixture was allowed to cool and filtered using a Buchner funnel and a 74-micrometer opening nylon mesh screen. The derivatized pulp remaining on the screen was washed four times with 100-ml to 150-ml portions of 2-propanol. The acidic reaction conditions resulted in a derivatized cellulose having a D.S. of 0.16 and the basic reaction conditions gave a derivatized cellulose having a D.S. of 0.12.

EXAMPLE 6

The preparation of a cellulose derivatized with aconitic epoxide is described in this example.

Preparation of Aconitic Epoxide

A one-liter, three-necked, round-bottomed flask equipped with a mechanical stirrer, addition funnel, reflux condenser, and thermometer was charged with 50 g (0.3 mole) of trans-aconitic acid (Aldrich Chemical Company, Inc.), 10 g (10 mole of tungstic acid, and 715 ml of 1N aqueous sodium hydroxide (0.72 mole). The resulting mixture was stirred at 40° C. while 35 ml (0.31 mole) of a 30 percent hydrogen peroxide solution was added drop-wise. The reaction mixture then was heated at 85° C. for three hours, forming a clear solution. The solution was cooled to room temperature and treated with 75 ml of 1ON (0.75 mole) hydrochloric acid. The resulting solution was extracted with ether in a continuous extractor for three days. The ether extract was concentrated on a rotary evaporator under reduced pressure to give a yellow solid. The solid was recrystallized from 50/50 (v/v) acetone/methylene chloride to give 7.2 g of a white solid which was verified to be aconitic epoxide by melting point and infrared and mass spectrographic analyses.

Preparation of Aconitic Pulp

Pressed sheets of LL-19 wood pulp (Coosa Pines mill) were fiberized by mixing in a Waring® blender with 2-propanol to 2–5 percent solids. After filtering and air drying, 8.4 g (0.052 mole) of the pulp and 75 ml of 2-propanol were charged to a Helicone® mixer. A solution of 7.7 g (0.19 mole) of sodium hydroxide in 15 ml of water was added to the mixer while stirring at about 5 rpm. Stirring was continued while heating the kettle contents for 1.25 hours at 60° C. A solution of 9.8 g (0.052 mole) of aconitic epoxide in 25 ml of 2-propanol was added to the pulp mixture. Heating and stirring were continued for five hours, after which time an additional 0.8 g of sodium hydroxide was added to maintain the pH of the reaction mixture above 8. After heating for another 2.5 hours, the product was collected and rinsed four times in a Waringo blender with 2-propanol/water, with filtration after each rinse. The resulting derivatized pulp had a D.S. of 0.21 and an SRV Of 2.7 g/g.

The preparation of a large number of celluloses derivatized with 2,3-epoxysuccinic acid demonstrated that degrees of substitution can vary from 0.02 to 0.31. When the degree of substitution was in a range of from around 0.02 to about 0.2, saline retention values increased approximately logarithmically from about 1 g saline/g to about 12 g saline/g. However, when the D.S. was about 0.3, a discontinuity occurred and the derivatized cellulose became soluble in water (i.e., infinitely swellable). Consequently, crosslinking of the derivatized cellulose was carried out in an effort to provide high absorbency and reduce solubility. The crosslinking experiments are presented in the examples which follow.

EXAMPLE 7

A series of experiments to explore various organic crosslinking agents were conducted utilizing methods well known to those having ordinary skill in the art. The derivatized cellulose employed was prepared in accordance with Examples 2 or 3, had a D.S. of 0.3, and was completely water soluble. The results are summarized in Table 2. Water was employed as the solvent or reaction medium unless stated otherwise in the table.

TABLE 2

Summary of Results of Crosslinking Experiments

| Ex. | Crosslinking Agent | Mole % | Time[a] | T, °C. | SRV[b] | Percent Recovery |
|---|---|---|---|---|---|---|
| 7-1 | Glyoxal | 1.0 | — | R.T.[c] | 6.0 | 80 |
| 7-2 | Glyoxal | 1.0 | 2.5 | 110 | 2.8 | 92 |
| 7-3 | Glyoxal | 3.5 | 2.5 | 110 | 2.3 | 84 |
| 7-4 | Glyoxal | 3.4 | 2.5 | 150 | 5.6 | 82 |
| 7-5 | Glyoxal | 3.3 | 9.0 | 150 | 1 | — |
| 7-6 | Glutaric Dialdehyde | 10.0 | 90 | 140 | 1.6 | 85 |
| 7-7[d] | Polyethylene glycol[e] diglycidyl ether | 3.1 | 480 | 82 | 11.7 | 14 |
| 7-8[f] | Polyethylene glycol[e] diglycidyl ether | 3.9 | 330[g] | 65–110 | 15.0 | 25 |
| 7-9 | 1,3-Dichloro-2-propanol | 15.6 | 15 | 140 | — | 0 |
| 7-10 | Aluminum potassium sulfate | 4.2 | — | R.T. | 7.0 | — |
| 7-11 | Tyzor Tetra-isopropyl titanate | 7.1 | 60 | 140 | — | 0 |

[a]In minutes.
[b]In g saline/g.
[c]Room temperature.
[d]In 2-propanol
[e]Molecular weight 600.
[f]At 65° C. for 180 minutes and 110° C. for 150 minutes.
[g]In methanol.

Based on the data in Table 2, with one exception, the methods studied were not especially noteworthy. However, polyethylene glycol diglycidyl ether resulted in significant saline retention values, although the yields of crosslinked, derivatized cellulose were low.

EXAMPLE 8

In view of the results obtained in Example 7, two other crosslinking methods were studied in some detail. These methods involved thermal crosslinking and the use of a trivalent metal compound, namely, monobasic aluminum acetate. This example describes the thermal crosslinking studies.

Thermal Crosslinking

The basic procedure for crosslinking with heat involved grinding a derivatized cellulose sample by means of a Brinkman table-top grinder with a 2.0-mm mesh opening. The resulting powder was sieved, and only the powder passing through a No. 35 mesh sieve (500-micrometer openings) was used. The powder was spread on a glass petri dish and placed in a preheated oven. At varying times, a portion of the powder was removed from the oven, weighed (to record the oven-dry weight), and stored in an aluminum pan until tested for its saline retention value and percent recovery.

The variables studied were crosslinking temperature, crosslinking time, and the degree of neutralization of the carboxylic acid groups on the derivatized cellulose. Neutralization involved taking a weighed sample of the sodium salt form (i.e., 100 percent neutralized) of the derivatized cellulose, dispersing or dissolving the sample in distilled water, adding the calculated amount of 1N hydrochloric acid to achieve the desired degree of neutralization, and precipitating the partially neutralized sample with 2-propanol. For example, to achieve 50 percent (0.5) neutralization of a sample having a D.S. of 0.3, the amount of hydrochloric acid required would be calculated as follows:

$$\text{meq HCl} = (0.5)(2.81\text{meq/g})(\text{sample wt.})$$

where 0.5 represents 50 percent neutralization and 2.81 is the number of milliequivalents of carboxylic acid groups per g of derivatized cellulose. With 1N hydrochloric acid, the required milliequivalents of HCl is the volume in ml of the acid solution which is required.

Thus, the derivatized cellulose sample, e.g. 0.75 g, was placed in a beaker with 8 ml of distilled water and the calculated volume of 1 N hydrochloric acid, e.g. 1.06 ml. The resulting slurry was mixed thoroughly and the beaker was covered and allowed to stand at room temperature. After three hours, the partially neutralized derivatized cellulose sample was precipitated with about two times the volume of the slurry of 2-propanol and filtered onto a 20-micrometer nylon mesh. The filtered product was rinsed twice with 2-propanol. After air-drying, the sample was ground, sieved, and thermally crosslinked as described above.

The results of the thermal crosslinking studies are summarized in Table 3.

TABLE 3

Summary of Thermal Crosslinking Studies

| Ex. | % Neut.[a] | T, °C. | Time[b] | SRV[c] | Percent Recovery |
|---|---|---|---|---|---|
| 8-1 | 100 | 150 | 300 | 11.0 | 54 |
| 8-2 | 100 | 150 | 360 | 16.6 | 13 |
| 8-3 | 100 | 150 | 480 | 10.4 | 59 |
| 8-4 | 100 | 150 | 600 | 9.4 | 60 |
| 8-5 | 100 | 150 | 930 | 5.5 | — |
| 8-6 | 0 | 150 | 2 | 3.7 | 69 |
| 8-7 | 0 | 150 | 5 | 4.6 | 62 |
| 8-8 | 0 | 150 | 15 | 0.9 | 84 |
| 8-9 | 80 | 150 | 15.2 | 10.2 | 45 |
| 8-10 | 80 | 150 | 35 | 7.0 | 70 |
| 8-11 | 80 | 150 | 67 | 6.0 | 73 |
| 8-12 | 80 | 150 | 100 | 5.5 | 71 |
| 8-13 | 80 | 150 | 120 | 4.2 | 52 |
| 8-14 | 80 | 150 | 180 | 3.7 | 79 |
| 8-15 | 100 | 150 | 300 | 4.8 | 36 |
| 8-16 | 100 | 150 | 480 | 3.4 | 43 |
| 8-17 | 100 | 150 | 618 | 4.6 | 39 |
| 8-18 | 80 | 150 | 14 | 9.7 | 5 |
| 8-19 | 80 | 150 | 20.2 | 9.3 | 11 |
| 8-20 | 80 | 150 | 45 | 9.8 | 38 |
| 8-21 | 80 | 130 | 2 | 12.1 | 4 |
| 8-22 | 80 | 130 | 4.7 | 11.8 | 10 |
| 8-23 | 80 | 130 | 6 | 11.7 | 14 |
| 8-24 | 80 | 130 | 11 | 10.8 | 10 |
| 8-25 | 80 | 130 | 15 | 11.3 | 27 |
| 8-26 | 80 | 130 | 20 | 11.1 | 30 |
| 8-27 | 80 | 130 | 25 | 10.7 | 34 |
| 8-28 | 50 | 130 | 2 | — | 0 |
| 8-29 | 50 | 130 | 9 | 10.0 | 12 |
| 8-30 | 50 | 130 | 30 | 5.9 | 27 |
| 8-31 | 50 | 130 | 60 | 1.3 | — |
| 8-32 | 50 | 130 | 120 | 3.4 | 18 |
| 8-33 | 50 | 130 | 300 | 3.6 | 49 |
| 8-34 | 50 | 130 | 515 | 1.0 | 77 |
| 8-35 | 50 | 130 | 2 | — | 0 |
| 8-36 | 50 | 130 | 4.3 | 18.3 | 20 |
| 8-37 | 50 | 130 | 8.2 | 15.3 | 50 |
| 8-38 | 0 | 130 | 2 | — | 0 |
| 8-39 | 0 | 130 | 5 | 5.1 | 61 |
| 8-40 | 0 | 130 | 8.2 | 3.8 | 73 |
| 8-41 | 0 | 130 | 11 | 3.4 | — |
| 8-42 | 0 | 130 | 14 | 2.2 | 78 |
| 8-43 | 0 | 130 | 20 | 1.5 | — |
| 8-44 | 50 | 110 | 2 | 2.6 | 15 |
| 8-45 | 50 | 110 | 5 | 1.6 | 65 |
| 8-46 | 50 | 110 | 8 | 2.5 | 72 |
| 8-47 | 50 | 110 | 15 | 2.9 | 73 |
| 8-48 | 50 | 110 | 30 | 3.0 | 41 |

[a]Percent neutralized.
[b]In minutes.
[c]Saline retention value in g saline/g.

The data in Table 3 indicate that, for the derivatized cellulose studied, 5 optimum conditions for increasing absorbency by means of thermal crosslinking appeared to utilize a crosslinking temperature of 130° C. for 4–8 minutes with 50 percent neutralization of the carboxylic acid groups present in the derivatized cellulose, although percent recovery values often were low. Increased crosslinking times typically had an adverse effect on absorbency and often resulted in increased yields.

EXAMPLE 9

This example describes the crosslinking studies with aluminum acetate.

As in the thermal crosslinking studies (Example 8), the derivatized cellulose employed was the water-soluble pulp derivatized with 2,3-epoxysuccinic acid and having a D.S. of 0.3. A typical procedure involved dissolving 0.42 g (oven-dry basis) of the pulp in sodium salt or 100 percent neutralized form in 19.64 g of water to obtain a 2.1 percent by weight solution. A 2.38-g portion of the solution, equivalent to 0.05 g of pulp on an oven-dry basis, was placed in a 25-ml glass vial. Then, 0.0024 g (0.0148 mmole 4.8 percent by weight) of monobasic aluminum acetate was weighed into a polystyrene weigh boat and added in one portion to the solution in the glass vial. The resulting viscous solution was thoroughly mixed with a spatula to break up and disperse the aluminum acetate powder. The solution was stirred for three days with a magnetic stir bar; the sample appeared to have fully gelled in one day. Approximately three volumes of 2-propanol was added to the vial to precipitate the crosslinked product. The product was collected on a Spectromesh filter using a Buchner funnel and rinsed three times with 50/50 water/2-propanol. Rinsing was carried out by mixing the product with one volume (about 2.5 ml) of distilled water for approximately two minutes, then adding one volume (about 2.5 ml) of 2-propanol to precipitate the product, and filtering after each rinse. The product then was rinsed with about 2.5 ml of 2-propanol, filtered, and air dried in a weigh boat.

The results are summarized in Table 4.

TABLE 4

Summary of Aluminum Acetate Crosslinking Studies

| | Pulp | Alum. Acetate | | Gelation | | Percent |
|---|---|---|---|---|---|---|
| Ex. | Conc.[a] | Wt. % | Mole % | Time[b] | SRV[c] | Recovery |
| 9-1 | 0.8 | 8.1 | 10.7 | 3 | 13.4 | 86 |
| 9-2 | 1.2 | 7.9 | 10.5 | 2 | 12.8 | 82 |

TABLE 4-continued

Summary of Aluminum Acetate Crosslinking Studies

| Ex. | Pulp Conc.[a] | Alum. Acetate Wt. % | Mole % | Gelation Time[b] | SRV[c] | Percent Recovery |
|---|---|---|---|---|---|---|
| 9-3 | 2.1 | 3.0 | 4.0 | 1 | 16.9 | 36 |
| 9-4 | 2.1 | 3.0 | 4.0 | 2 | 14.2 | 73 |
| 9-5 | 2.1 | 4.8 | 6.4 | 3 | 17.0 | 86 |
| 9-6 | 1.0 | 21.0 | 27.0 | — | 1.3 | 32 |
| 9-7 | 1.0 | 22.0 | 29.0 | — | 2.9 | 35 |
| 9-8 | 2.5 | 2.6 | 3.5 | — | — | 0 |
| 9-9 | 2.5 | 4.0 | 5.3 | — | 10.8 | 3 |
| 9-10 | 2.5 | 4.0 | 5.3 | — | 15.4 | 4 |
| 9-11 | 2.5 | 6.7 | 8.8 | — | 11.4 | 25 |
| 9-12 | 2.5 | 20.0 | 26.0 | — | 3.8 | 67 |

[a]In weight percent.
[b]In days
[c]Saline retention value in g saline/g.

As Table 4 illustrates, adequate treatment with monobasic aluminum acetate renders 5 the water-soluble derivatized pulp absorbent and less soluble. Example 9-5 illustrates a desired embodiment of aluminum acetate crosslinking, in which absorbency was increased to 17.0 g saline/g with 86 percent recovery.

EXAMPLE 10

Both the aluminum acetate and thermal crosslinking methods were found to be reversible. That is, the insoluble crosslinked pulps could be rendered water soluble (or at least water dispersible) with a simple chemical treatment. Accordingly, such crosslinked materials may be useful as a flushable absorbent material. This example illustrates the reversibility of such crosslinking methods.

Reversal of Aluminum Crosslinking

A 2,3-epoxysuccinic acid-derivatized pulp which had been crosslinked with 10.7 mole percent aluminum (Example 9-1) was used in the experiment. A 0.06-g portion of the pulp, which had been recovered after an SRV test, was rinsed with about 10 ml of 2-propanol, filtered, rinsed with about 10 ml of water while still on the filtration medium to remove sodium chloride derived from the SRV test, and then rinsed with about 20 ml of 2-propanol. The pulp then was air dried. Initially, the crosslinked pulp had contained 0.0045 g (0.028 mmole) of aluminum acetate. Consequently, a 5.3-fold molar excess, or 0.55 g (0.148 mmole) of ethylenediamine tetraacetic acid, disodium salt dihydrate in 10 ml of water was added to the dried pulp. The resulting pulp slurry was stirred in a beaker with a magnetic stir bar. After about three hours, the pulp had dispersed thoroughly so that only very small particles were visible to the naked eye. Sodium phosphate dodecahydrate was also investigated, but did not seem to disperse the pulp as well, after a twenty-fold excess of the reagent had been added to the pulp.

Reversal of Thermal Crosslinking

The crosslinked pulp of Example 8-5, in the sodium salt form, was employed. A 0.10-g portion of the pulp was placed in a beaker with about 25-ml of 0.1N sodium hydroxide solution and stirred with a magnetic stir bar. After about three hours, the pulp had dissolved in the basic solution.

While the specification has been described in detail with respect to specific embodiments thereof, it will be appreciated by those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A derivatized polysaccharide comprising:
a polysaccharide in which at least a portion of the active hydrogens originally present in the polysaccharide are substituted by monovalent aliphatic groups containing at least two carboxylic acid groups to an extent sufficient to provide a degree of substitution of at least about 0.1, wherein the monovalent aliphatic groups contain from 4 to about 10 carbon atoms and the substitution results from the reaction of an epoxy group in an aliphatic polycarboxylic acid with the active hydrogens originally present in the polysaccharide.

2. The derivatized polysaccharide of claim 1, in which the polysaccharide is cellulose.

3. The derivatized polysaccharide of claim 1, in which at least a portion of the carboxylic acid groups present therein are crosslinked.

4. The derivatized polysaccharide of claim 3, in which at least a portion of the carboxylic acid groups present therein are reversibly crosslinked.

5. The derivatized polysaccharide of claim 1, in which the monovalent aliphatic groups containing at least two carboxylic acid groups are derived from 2,3-epoxysuccinic acid, 1,2-epoxypropane-1,2,3-tricarboxylic acid, or 2-(epoxyethyl)succinic acid.

6. A method of preparing a derivatized polysaccharide, the method comprising:
providing a polysaccharide;
dispersing the polysaccharide in a strongly alkaline aqueous alcohol solution;
adding to the dispersion an excess of an aliphatic polycarboxylic acid having an epoxy group, wherein the aliphatic polycarboxylic acid contains from 4 to about 10 carbon atoms; and
heating the dispersion at a temperature and for a time sufficient to permit the reaction of epoxy groups of the aliphatic polycarboxylic acid with active hydrogens present in the polysaccharide to an extent sufficient to result in a degree of substitution of at least about 0.1.

7. The method of claim 6, in which the polysaccharide is cellulose.

8. The method of claim 6, in which the aliphatic polycarboxylic acid containing an epoxy groups is 2,3-epoxysuccinic acid, 1,2-epoxypropane-1,2,3-tricarboxylic acid, or 2-(epoxyethyl)succinic acid.

9. The method of claim 6 which further comprises at least partially neutralizing the strongly alkaline aqueous alcohol solution after the heating step.

10. The method of claim 6 which further comprises washing the derivatized polysaccharide with an aqueous alcohol solution.

11. The method of claim 10 which further comprises adjusting the pH of an aqueous alcohol dispersion of the derivatized polysaccharide to a value of from about 4 to about 9.

12. The method of claim 6 which further comprises crosslinking at least a portion of the carboxylic acid groups present in the derivatized polysaccharide.

13. The method of claim 12, in which crosslinking is carried out under conditions sufficient to render the crosslinks reversible.

14. The method of claim 13, in which crosslinking is accomplished by heat.

15. The method of claim 13, in which crosslinking is accomplished with a trivalent metal compound.

16. The method of claim 15, in which the trivalent metal compound is a monobasic aluminum acetate.

17. A paper containing an amount of the derivatized polysaccharide of claim 1 sufficient to improve the strength characteristics of said paper.

18. The paper of claim 17, in which the amount of derivatized cellulose present in the paper is in a range of from about 2 to about 35 percent by weight, based on the weight of the paper.

19. The paper of claim 17, in which at least a portion of the carboxylic acid groups present in the derivatized cellulose are crosslinked.

20. The paper of claim 17, in which at least a portion of the carboxylic acid groups present in the derivatized cellulose are reversibly crosslinked.

21. The paper of claim 17, in which the monovalent aliphatic groups containing at least two carboxylic acid groups are derived from 2,3-epoxysuccinic acid, 1,2-epoxypropane-1,2,3-tricarboxylic acid, or 2-(epoxyethyl)succinic acid.

* * * * *